(12) United States Patent
Defreitas et al.

(10) Patent No.: US 10,456,213 B2
(45) Date of Patent: *Oct. 29, 2019

(54) TOMOSYNTHESIS-GUIDED BIOPSY APPARATUS AND METHOD

(71) Applicant: Hologic, Inc., Marlborough, MA (US)

(72) Inventors: Kenneth F. Defreitas, Patterson, NY (US); Ian Shaw, Yorktown Heights, NY (US); John Laviola, Orange, CT (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/127,564

(22) Filed: Sep. 11, 2018

(65) Prior Publication Data

US 2019/0015173 A1    Jan. 17, 2019

Related U.S. Application Data

(63) Continuation of application No. 14/777,199, filed as application No. PCT/US2014/026164 on Mar. 13, 2014, now Pat. No. 10,092,358.

(Continued)

(51) Int. Cl.
*A61B 6/02*    (2006.01)
*A61B 90/11*    (2016.01)
(Continued)

(52) U.S. Cl.
CPC .............. *A61B 90/11* (2016.02); *A61B 6/025* (2013.01); *A61B 6/0414* (2013.01);
(Continued)

(58) Field of Classification Search
CPC .......... A61B 10/0233; A61B 2010/045; A61B 6/025; A61B 6/0414; A61B 6/0435;
(Continued)

(56) References Cited

U.S. PATENT DOCUMENTS

| 4,821,727 A | 4/1989 | Levene et al. |
| 5,078,142 A | 1/1992 | Siczek et al. |

(Continued)

FOREIGN PATENT DOCUMENTS

| EP | 2236085 | 6/2010 |
| EP | 1986548 | 1/2013 |

(Continued)

OTHER PUBLICATIONS

"Filtered Back Projection", (NYGREN), published May 8, 2007, URL: http://web.archive.org/web/19991010131715/http://www.owlnet.rice.edu/~elec539/Projects97/cult/node2.html, 2 pgs.

(Continued)

*Primary Examiner* — Ruth S Smith

(57) ABSTRACT

A station for tomotactic-guided biopsy in prone includes a table with an aperture, and a tomosynthesis imaging system. A biopsy gun can be mounted on a stage arm assembly disposed below the table. The imaging system and stage arm assembly can be independently rotated and linearly repositioned in one or more dimensions, thereby allowing the tomotactic scan axis to be located relative to a breast being imaged.

20 Claims, 8 Drawing Sheets

Biopsy Station 100

Related U.S. Application Data

(60) Provisional application No. 61/787,825, filed on Mar. 15, 2013.

(51) Int. Cl.
    *A61B 6/04* (2006.01)
    *A61B 6/00* (2006.01)
    A61B 6/12 (2006.01)
    A61B 10/02 (2006.01)
    A61B 10/04 (2006.01)

(52) U.S. Cl.
    CPC ............ *A61B 6/0435* (2013.01); *A61B 6/502* (2013.01); *A61B 6/12* (2013.01); *A61B 6/4452* (2013.01); *A61B 10/0233* (2013.01); *A61B 2010/045* (2013.01)

(58) Field of Classification Search
    CPC ......... A61B 6/12; A61B 6/4452; A61B 6/502; A61B 90/11
    See application file for complete search history.

(56) References Cited

U.S. PATENT DOCUMENTS

| | | | |
|---|---|---|---|
| 5,129,911 A | 7/1992 | Siczek et al. | |
| 5,219,351 A | 6/1993 | Teubner | |
| 5,240,011 A | 8/1993 | Assa | |
| 5,280,427 A | 1/1994 | Magnusson | |
| 5,289,520 A | 2/1994 | Pellegrino et al. | |
| 5,386,447 A | 1/1995 | Siczek | |
| 5,415,169 A | 5/1995 | Siczek et al. | |
| 5,426,685 A | 6/1995 | Pellegrino et al. | |
| 5,594,769 A | 1/1997 | Pellegrino et al. | |
| 5,609,152 A | 3/1997 | Pellegrino et al. | |
| 5,735,264 A | 4/1998 | Siczek et al. | |
| 5,769,086 A | 6/1998 | Ritchart et al. | |
| 5,773,832 A | 6/1998 | Sayed et al. | |
| 5,803,912 A | 9/1998 | Siczek et al. | |
| 6,022,325 A | 2/2000 | Siczek et al. | |
| 6,101,236 A | 8/2000 | Wang et al. | |
| 6,102,866 A | 8/2000 | Nields et al. | |
| 6,245,028 B1 | 6/2001 | Furst et al. | |
| 6,293,282 B1 | 9/2001 | Lemelson | |
| 6,459,925 B1 | 10/2002 | Nields et al. | |
| 6,468,226 B1 | 10/2002 | McIntyre, IV | |
| 6,480,565 B1 | 11/2002 | Ning | |
| 6,620,111 B2 | 9/2003 | Stephens et al. | |
| 6,626,849 B2 | 9/2003 | Huitema et al. | |
| 6,638,235 B2 | 10/2003 | Miller et al. | |
| 6,758,824 B1 | 7/2004 | Miller et al. | |
| 6,987,331 B2 | 1/2006 | Koeppe | |
| 7,123,684 B2 | 10/2006 | Jing et al. | |
| 7,466,795 B2 | 12/2008 | Eberhard et al. | |
| 7,697,660 B2 | 4/2010 | Ning | |
| 7,787,936 B2 | 8/2010 | Kressy | |
| 7,831,296 B2 | 11/2010 | DeFreitas et al. | |
| 7,869,563 B2 | 1/2011 | DeFreitas | |
| 8,532,745 B2 | 9/2013 | DeFreitas et al. | |
| 10,092,358 B2 * | 10/2018 | Defreitas ............... A61B 6/025 | |
| 2001/0038681 A1 | 11/2001 | Stanton et al. | |
| 2002/0113681 A1 | 8/2002 | Byram | |
| 2003/0018272 A1 | 1/2003 | Treado et al. | |
| 2003/0073895 A1 | 4/2003 | Nields et al. | |
| 2003/0135115 A1 | 7/2003 | Burdette et al. | |
| 2004/0077938 A1 | 4/2004 | Mark et al. | |
| 2004/0081273 A1 | 4/2004 | Ning | |
| 2004/0171933 A1 | 9/2004 | Stoller et al. | |
| 2004/0171986 A1 | 9/2004 | Tremaglio, Jr. et al. | |
| 2004/0267157 A1 | 12/2004 | Miller et al. | |
| 2005/0049521 A1 | 3/2005 | Miller et al. | |
| 2005/0089205 A1 | 4/2005 | Kapur | |
| 2005/0113681 A1 | 5/2005 | DeFreitas et al. | |
| 2005/0113715 A1 | 5/2005 | Schwindt et al. | |
| 2005/0124845 A1 | 6/2005 | Thomadsen et al. | |
| 2006/0009693 A1 | 1/2006 | Hanover et al. | |
| 2006/0030784 A1 | 2/2006 | Miller et al. | |
| 2006/0098855 A1 | 5/2006 | Gkanatsios et al. | |
| 2006/0129062 A1 | 6/2006 | Nicoson et al. | |
| 2006/0155209 A1 | 6/2006 | Miller et al. | |
| 2006/0257009 A1 | 11/2006 | Wang | |
| 2007/0225600 A1 | 9/2007 | Weibrecht et al. | |
| 2007/0263765 A1 | 11/2007 | Wu | |
| 2008/0045833 A1 | 2/2008 | DeFreitas et al. | |
| 2008/0187095 A1 | 8/2008 | Boone et al. | |
| 2008/0198966 A1 | 8/2008 | Hjarn | |
| 2009/0003519 A1 | 1/2009 | DeFreitas | |
| 2009/0080604 A1 | 3/2009 | Shores et al. | |
| 2009/0143674 A1 | 6/2009 | Nields | |
| 2009/0171244 A1 | 7/2009 | Ning | |
| 2010/0034348 A1 | 2/2010 | Yu | |
| 2010/0098214 A1 | 4/2010 | Star-Lack et al. | |
| 2011/0087132 A1 | 4/2011 | DeFreitas et al. | |
| 2011/0182402 A1 | 7/2011 | Partain | |
| 2011/0237927 A1 | 9/2011 | Brooks et al. | |
| 2014/0073913 A1 | 3/2014 | DeFreitas et al. | |
| 2016/0022364 A1 | 1/2016 | DeFreitas et al. | |
| 2018/0256118 A1 | 9/2018 | DeFreitas | |

FOREIGN PATENT DOCUMENTS

| | | |
|---|---|---|
| WO | WO 93/17620 | 9/1993 |
| WO | WO 94/06352 | 3/1994 |
| WO | WO 1997/00649 | 1/1997 |
| WO | WO 00/51484 | 9/2000 |
| WO | WO 2005/110230 | 11/2005 |
| WO | WO 2005/112767 | 12/2005 |
| WO | WO 2006/055830 | 5/2006 |
| WO | WO 2006/058160 | 6/2006 |
| WO | 2008/014670 | 2/2008 |
| WO | WO 08/014670 | 2/2008 |
| WO | WO 2008/054436 | 5/2008 |
| WO | WO 2012/068373 | 5/2012 |
| WO | WO 2012/112627 | 8/2012 |

OTHER PUBLICATIONS

European Extended Search Report for European Patent Application No. 14770362.3 dated Sep. 28, 2016, 8 pgs.

European extended Search Report in Application 18153706.9, dated Jun. 1, 2018, 8 pages.

Hologic, "Lorad StereoLoc II" Operator's Manual 9-500-0261, Rev. 005, 2004, 78 pgs.

Observations by Third Party, Remarks concerning European patent application No. 10707751.3 according to Article 115 EPC, dated Apr. 24, 2014, 8 pgs.

PCT International Search Report in Application PCT/US2014/026164, dated Jul. 28, 2014, 2 pgs.

PCT International Written Report for International Application PCT/US2014/026164, dated Jul. 28, 2014, 12 pgs.

Shrading, Simone et al., "Digital Breast Tomosynthesls-gulded Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.

* cited by examiner

Biopsy Station 100

TOMOSYNTHESIS-GUIDED BIOPSY APPARATUS AND METHOD

CROSS REFERENCE TO RELATED APPLICATIONS

This application is a continuation of U.S. patent application Ser. No. 14/777,199, filed Sep. 15, 2015, now U.S. Pat. No. 10,092,358, which is a National Stage Entry application of PCT International Patent Application No. PCT/US2014/026164, filed Mar. 13, 2014, and claims priority to U.S. Provisional Patent Application Ser. No. 61/787,825, filed Mar. 15, 2013, the disclosures of which are hereby incorporated by reference in their entirety into the present application.

BACKGROUND

The subject matter of this disclosure is generally related to the medical field. Medical imaging technologies such as stereotactic x-ray, fluoroscopy, computer tomography, ultrasound, nuclear medicine and magnetic resonance imaging enable detection of small abnormalities in the body of a patient. The discovery of certain abnormalities may prompt performance of a biopsy procedure to obtain a tissue sample for lab analysis to help diagnose and treat patients suspected of having cancerous tumors, pre-malignant conditions or other diseases or disorders. The biopsy may be either an open surgical procedure or a percutaneous procedure. Percutaneous biopsy is often preferable to an open surgical biopsy in the case of small abnormalities located deep within the body because a percutaneous biopsy removes a relatively small amount of tissue. For example, a biopsy needle can be used to remove individual cells or clusters of cells in the case of fine needle aspiration (FNA), and a core or fragment of tissue in the case of a core biopsy.

A biopsy gun and guidance system may be used to move the biopsy needle with precision along a planned path in order to obtain a suitable sample of the abnormality. An example of a stereotactic guided lateral arm system is disclosed in U.S. Published Patent Application 2001/0087132 A1, Ser. No. 12/715,591, titled NEEDLE BREAST BIOPSY SYSTEM AND METHOD FOR USE, which is incorporated by reference. In order to perform a biopsy procedure the breast is placed in compression and multiple x-ray images are used to localize the abnormality and perform final adjustments of the needle guidance system. One technological challenge in designing guided biopsy systems is that the biopsy needle may create undesirable artifacts in the images. For example, in a configuration where the biopsy needle is aligned with the path between the x-ray source and x-ray detector a portion of the needle may reside in the path and consequently be imaged. Another technological challenge is accommodation of relatively thin breasts. A "side entry" may be the only practical option for biopsy of a thin breast under compression. The lateral arm may be detached and reattached in order to set up for such a procedure. However, various manual calculations may be required in order to prepare for the procedure and the breast platform or x-ray detector may interfere with the path of the biopsy gun due to space limitations. These technological challenges may become even more complex if tomotactic guidance is used rather than stereotactic guidance. Tomotactic guidance is based on tomosynthesis imaging. A s disclosed in U.S. Published Patent Application 2008/0045833 A1, Ser. No. 11/707,587, titled BREAST BIOPSY AND NEEDLE LOCALIZATION USING TOMOSYN- THESSIS SYSTEMS, which is incorporated by reference, exposures at angles where the biopsy gun would cause artifacts to appear in the image can be skipped. In general, however, a breast biopsy system that would help solve some or all of these challenges would be desirable.

SUMMARY

According to an aspect an apparatus includes: a table for supporting a patient in a prone position; a tomosynthesis imaging system disposed below the table for imaging a breast of the patient; and a stage arm assembly which positions a biopsy needle to obtain a tissue sample from the portion of the patient imaged by the tomosynthesis imaging system.

According to another aspect a method includes: positioning a patient on a table in a prone position; imaging a portion of the patient with a tomosynthesis imaging system disposed below the table; positioning a biopsy needle by configuring a stage arm assembly using information from the tomosynthesis imaging system; and obtaining a tissue sample from the portion of the patient imaged by the tomosynthesis imaging system.

Advantages include simple and flexible set up. The table may have an aperture through which the breast undergoing biopsy extends with the patient in a prone position. Non-limiting examples of known prone approaches for imaging and/or biopsy include PCT Publication No. WO 2012/112627, U.S. Patent Application Publication Nos. 2009/0080604 and 2009/171244, and U.S. Pat. Nos. 6,480,565, 6,987,331, and 7,697,660, each of which is incorporated by reference herein in their entireties. Moreover, the aperture may be disposed approximately midway along the length of the table so that the table may accommodate 180 degree repositioning of the patient. The stage arm assembly and imaging system may be independently rotatable for set up, e.g., each through a 180° range of arc, without being detached and reattached or using optional parts. Various linear adjustments may also be possible. Consequently, the breast of a patient in a prone position can be accessed through a range of 360 degrees in various planes via a combination of reversing the position of the patient and simple rotational and linear adjustments of the stage arm assembly and imaging system.

Another advantage is accommodation of relatively thin breasts. Due to the relative size and location of cutting features of the biopsy needle it may be necessary or desirable to perform a "side entry" biopsy procedure relative to the axis of compression. Certain aspects may allow use of a relatively small x-ray receptor that enables enhanced geometry of other features in order to reduce the possibility of interference with the biopsy gun. For example, the x-ray receptor and x-ray energy source may be mounted on a support structure such as a c-arm which maintains the source and receptor in alignment at a fixed distance during a scan or sweep such that both the detector and the receptor move arcuately, thereby allowing receptor size to be reduced. The detector may also be offset from a breast support platform by a distance on the order of several centimeters. Reduced receptor size and offset from the breast support platform allow reduction of the size of the surface supporting the breast. Reduction of the size of the supporting surface allows adjacent side-edge sections to be angled or curved away such that interference with the biopsy gun is avoided, thereby facilitating side entry biopsy of relatively thin breasts.

Another advantage is mitigation or elimination of image artifacts caused by the biopsy needle. The stage arm, and thus the gun mount and biopsy needle, may be oriented at a fixed inclination, e.g., 10°, relative to the plane in which the stage arm assembly is rotatable. Inclination of the stage arm allows a "zero degree" offset configuration in which the stage arm assembly is aligned with the imaging system. Optionally, the stage arm can be positioned on an axis offset from that of the imaging system. In particular, the inclined biopsy gun and needle reside above or below rather than in the field of view of the imaging system so the images are free of biopsy needle artifacts.

Unless specifically stated otherwise, the features described herein can be used in any combination, and the aspects can include any one or more of the embodiments. Moreover, other features and advantages will become apparent to those of ordinary skill in the art in view of the figures and detailed description.

DETAILED DESCRIPTION

Figure 1:
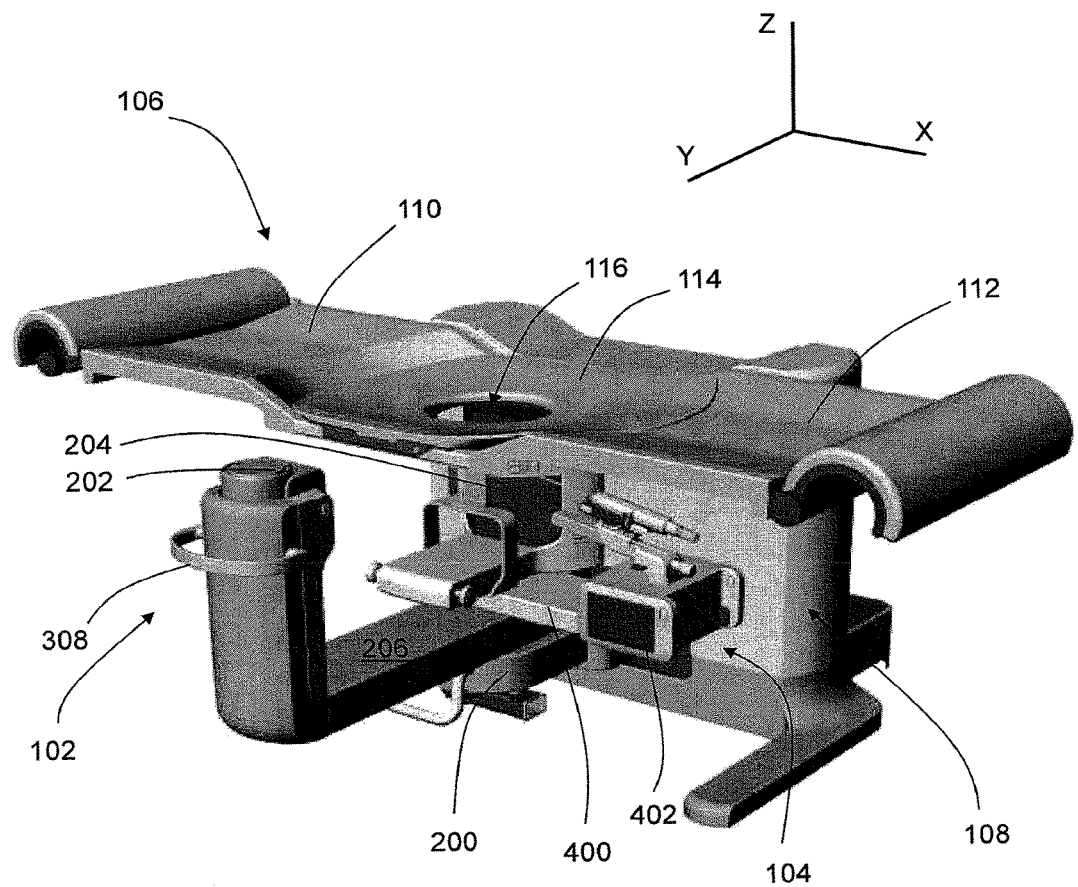
FIG. 1 is an isometric view of a tomotactic guided biopsy station.
Figure 2:
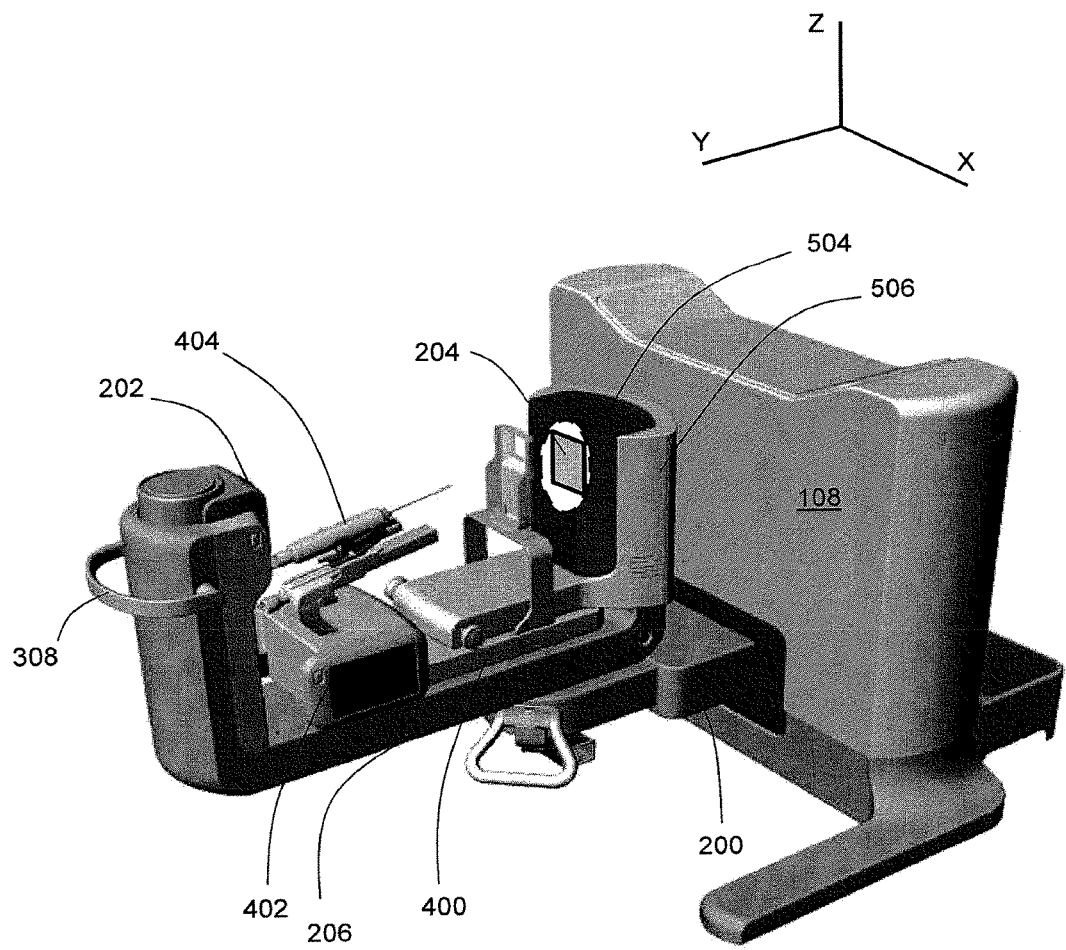
FIG. 2 illustrates the station of FIG. 1 in a zero degree offset configuration with the table top removed to better illustrate certain features such as the x-ray receptor which is shown via a cutaway of the breast platform.
Figure 3:
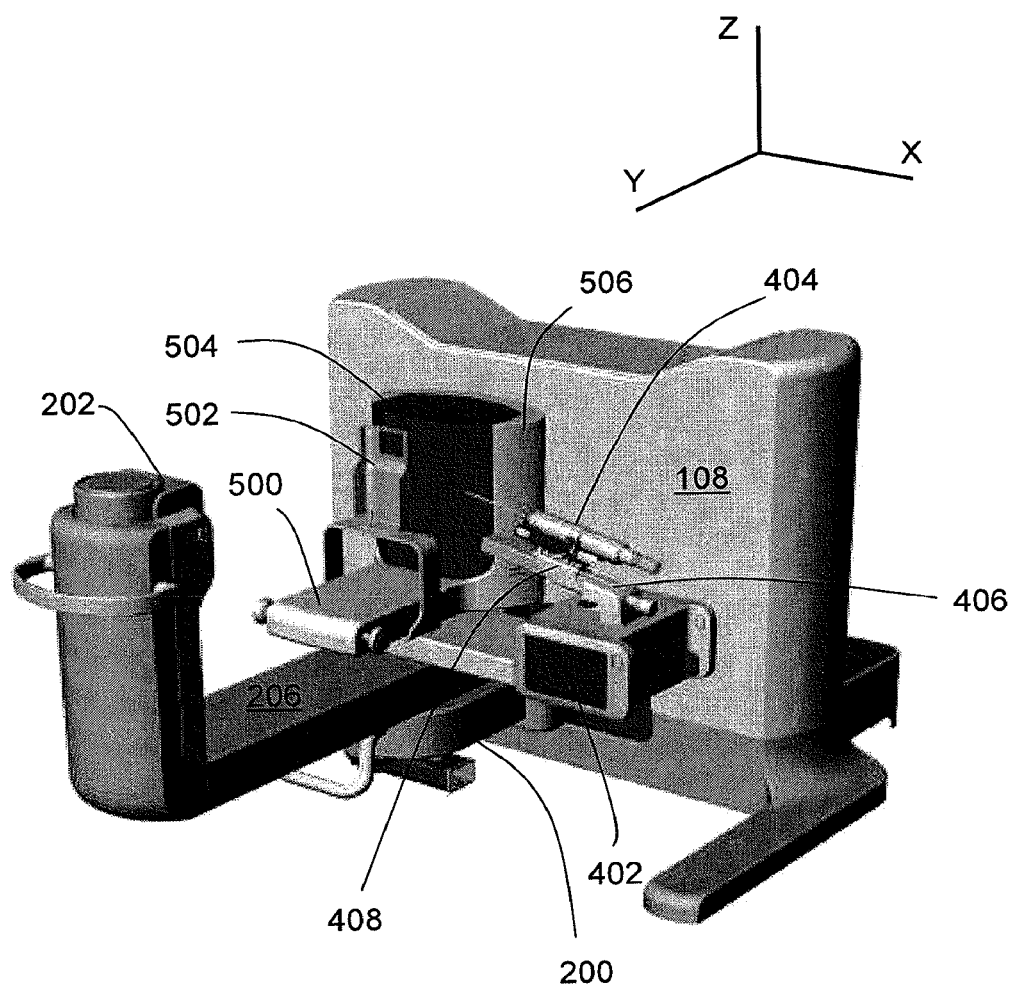
FIGS. 3-7 are various views of the station of FIG. 2 in a ninety degree offset configuration.
Figure 4:
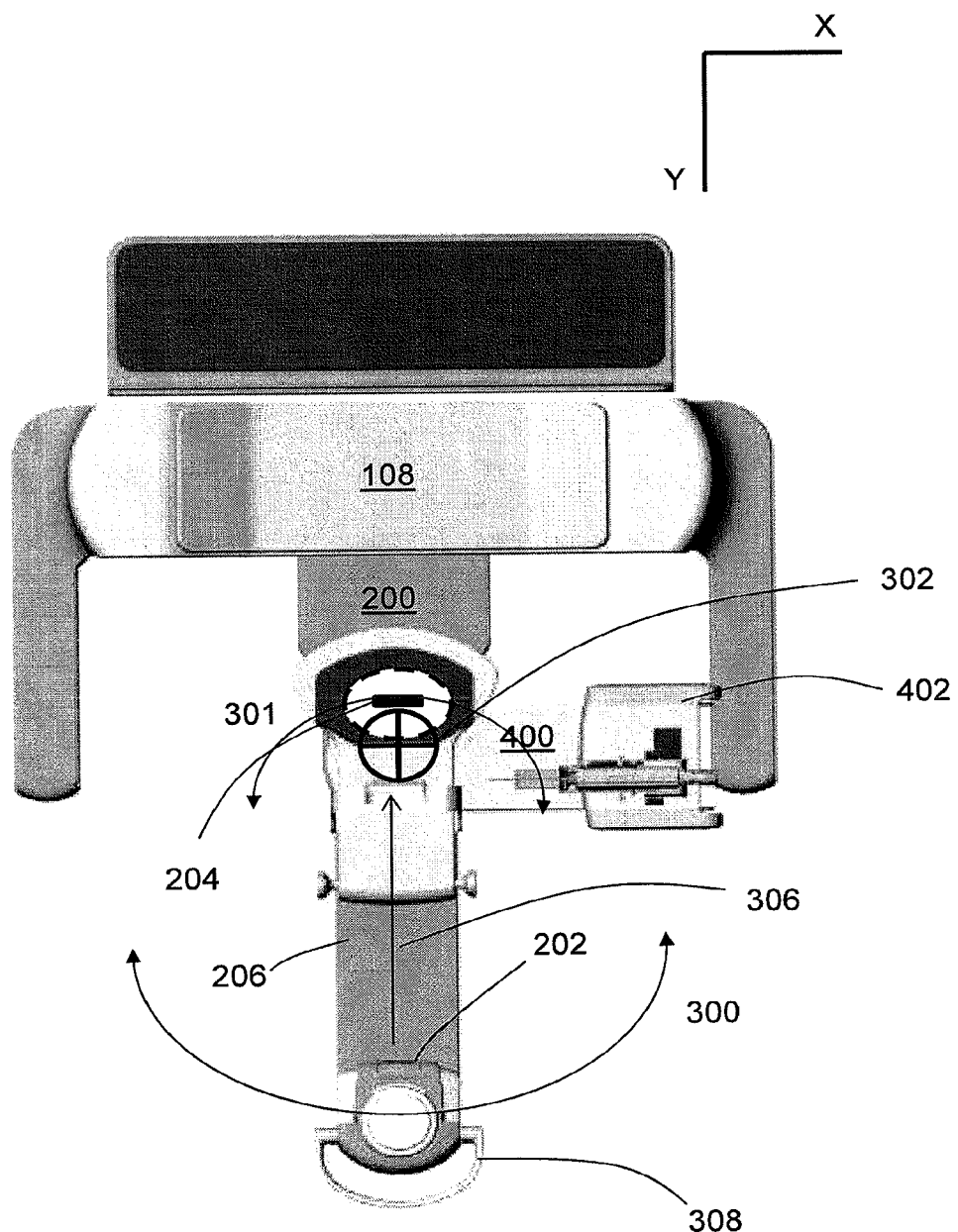
Figure 5:
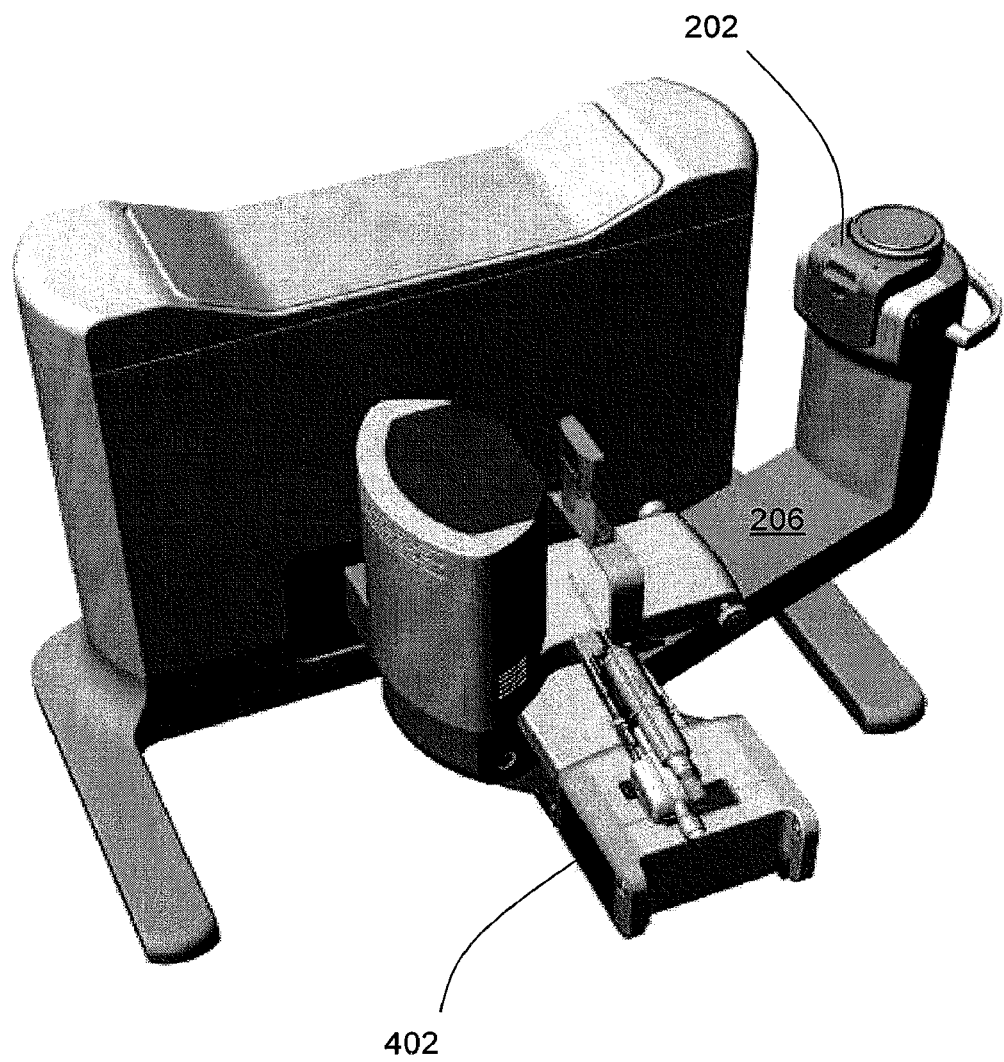
Figure 6:
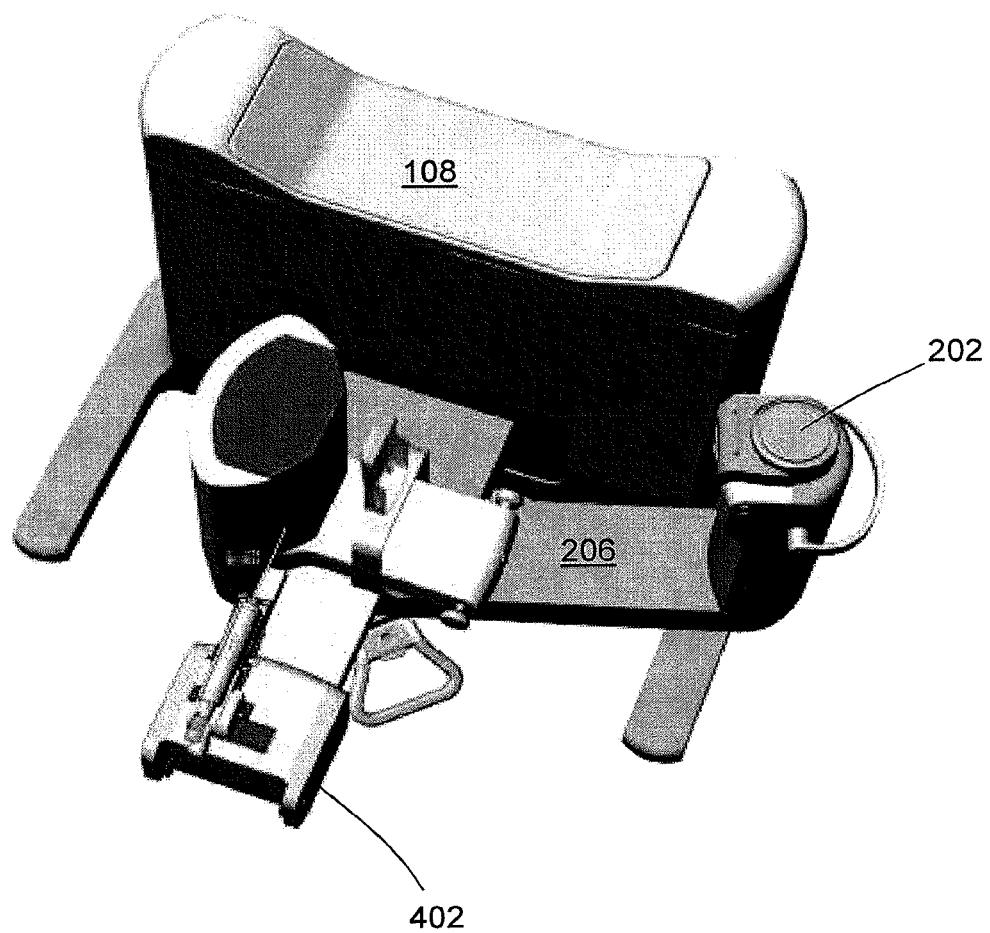
Figure 7:
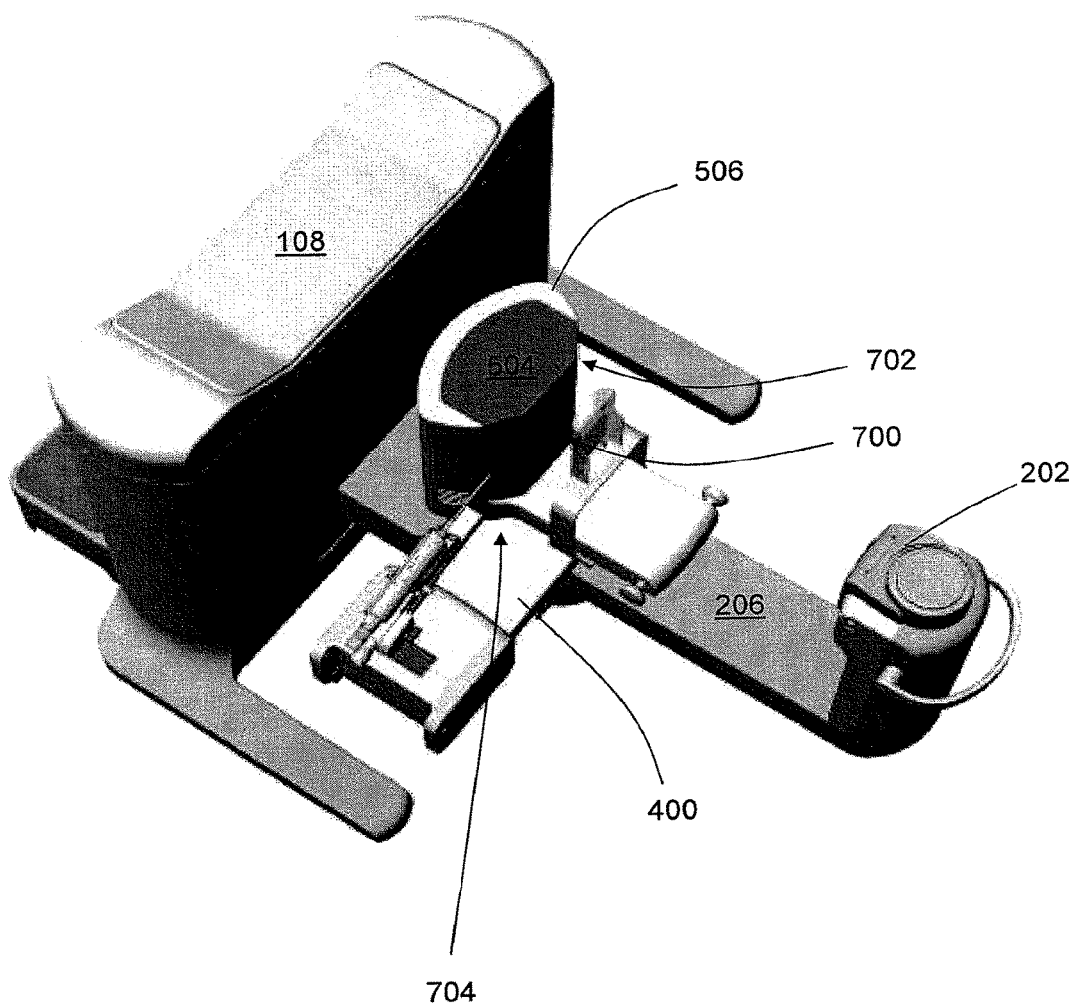

Referring to FIG. 1, a biopsy station 100 for performing tomotactic guided breast biopsy in prone may include a tomosynthesis imaging system 102 and a stage arm assembly 104 positioned below a biopsy table 106. The tomosynthesis imaging system and stage arm assembly are used for needle guidance. As explained in greater detail below, either or both the imaging system and stage arm assembly may be repositionable in one or more dimensions to facilitate the biopsy procedure. An example of a tomosynthesis imaging system is described in U.S. Pat. No. 7,869,563, which is hereby incorporated by reference, and sold commercially as Selenia® Dimensions® digital breast tomosynthesis system from Hologic, Inc. It should be noted, however, that the biopsy station is not limited to use with tomosynthesis imaging, and could utilize one or more of tomotactic, stereotactic, and other forms of guidance.

The biopsy table 106 is supported by a footed base 108. The base is offset to one side of the table such that an area beneath the table is available for positioning both a portion of the body of the patient on which the biopsy is performed and equipment for performing the biopsy. The table 106 includes a rigid platform which, may be cantilevered from the base 108, and which supports the patient during the biopsy procedure. The platform may be partially or wholly covered with padding for the comfort of the patient. The table may be contoured such that symmetrical distal end sections 110, 112 are elevated relative to a central section 114. Either of the elevated sections 110, 112 can help support the legs of the patient, thereby allowing 180 degree repositioning of the patient. The central section 114 supports the head, abdomen and hip of the patient. Transitions between the end sections and the central section are angled to provide comfortable head, abdomen and hip support. An aperture 116 in the central section 114 of the table enables a portion of the body of the patient to extend below the table when the patient is situated in a prone position. For example, the breast being biopsied may extend through the aperture. Other parts of the patient's body may also extend through the aperture, e.g., an arm, for enhanced comfort or positioning for the biopsy procedure. Some aspects of the table may be consistent with features described in International Application Number PCT/US11/61186, titled TABLE FOR PERFORMING MEDICAL PROCEDURES, filed Nov. 17, 2011, and U.S. Pat. No. 5,289,520, titled STEREOTACTIC MAMMOGRAPHY IMAGING SYSTEM WITH PRONE POSITION EXAMINATION TABLE AND CCD CAMERA, filed Oct. 6, 1992, both of which are incorporated by reference.

Referring now to FIGS. 1-7, an equipment support platform 200 is cantilevered from the base 108 beneath the table in the Y-dimension. The equipment support platform may be statically or repositionably connected to the base, and may move in a coordinated manner with, or independent of, the table based on settings which can be changed by an operator. The support platform may be connected to the base via a Y-axis slide assembly which enables the support platform to move relative to the base in the Y-dimension. An X-axis slide assembly may enable the support platform to move relative to the base in the X-dimension. Range of motion may be approximately +/−4 inches relative to a Z-axis defined by the center of the aperture. A handle connected to the support platform facilitates manual positioning of the platform by an operator. Slide lock features may be employed to secure the platform in a desired position.

The tomosynthesis imaging system 102 is mounted on the equipment support platform 200. The imaging system may include an x-ray energy source 202 and an x-ray energy receptor 204 (shown via cutaways in FIGS. 2 and 4). The source and receptor are aligned such that the receptor detects energy emitted by the source. The energy source 202 is positioned on a first upright portion of a support arm 206 such as a c-arm, and the energy receptor 204 is positioned on a second upright portion of the support arm. The support arm 206 helps maintain the receptor 204 and energy source 202 in alignment at a fixed distance, thereby mitigating or eliminating the need for focus adjustment. The support arm 206 is connected to the support platform 200 via a pivoting connector such as a bearing. As will be explained in greater detail below, during a scan or sweep the support arm moves under motor control such that the energy source 202 moves along an arc 300 (see FIG. 4 specifically) defined by a Z-axis of rotation 302 defined by a pivoting connector such as a bearing. The receptor 204 moves along an arc 301 characterized by a smaller radius than arc 300 because the pivoting connector via which the support arm is connected to the support platform is nearer to the second upright portion of the c-arm than the first upright portion of the c-arm. A handle 308 connected to the first upright portion facilitates manual rotational positioning of the support arm 206 within a 180 degree range of motion in the X-Y plane during set up by an operator. Consequently, a path 306 of x-ray energy defined between the energy source 202 and receptor 204 in the X-Y plane can be reoriented within the X-Y plane with respect to the patient's breast through the 180 degree range of motion during set up. Moreover, because the position of the patient can be reversed (changed 180 degrees horizontally in the X-Y plane), the biopsy needle is effectively positionable through 360 degrees in the X-Y plane relative to the breast.

The biopsy gun stage arm assembly 104 is connected to the support platform 200 via a pivoting connector such as a bearing. Moreover, the stage arm assembly may pivot around a Z-axis which is coincident with Z-axis 302, and a multi-part bearing assembly may be utilized to enable independent rotational movement of the imaging system and the stage arm assembly. Optionally, the stage arm assembly may rotate about an axis offset from that of the imaging system. A rotatable support platform 400 associated with the stage arm assembly is disposed above the support arm 206. The stage arm assembly is rotatable through 180 degrees in the X-Y plane for manual set up by the operator. The stage arm assembly may be secured against rotational movement by a brake mechanism, e.g., to inhibit motion during a sweep or scan. A guidance module 402 with an interface and display mounted in a housing integral with or connected to the support platform displays tomosynthesis images and information about the relative locations of the targeted feature and the biopsy gun 404 to help position the biopsy gun and guide its path of travel such that the needle intersects with the target feature. A stage arm 406 is disposed on top of the guidance module 402 housing. A carriage slide assembly 408 is connected to the stage arm. A gun mount is connected to the carriage slide assembly. A biopsy gun 404 is mounted to the gun mount. The stage arm assembly may be oriented such that the operational path of travel of the biopsy gun needle intersects the Z-axis 302 about which the stage arm assembly and support arm rotate. More particularly, the orientation of the stage arm assembly may be such that the operational path of travel of the biopsy gun needle intersects the Z-axis about which the stage arm assembly and support arm rotate at a particular point within the field of view of the tomosynthesis imaging system. The carriage slide assembly enables manual or motor-driven adjustment of the distance between the needle and the rotational Z-axis intersection point. The stage arm (and thus the gun mount and biopsy needle) may be oriented at a fixed inclination, e.g., 10°, relative to the X-Y plane in which the stage arm assembly is rotatable. Inclination of the stage arm allows a "zero degree" offset configuration in which the stage arm assembly is aligned with the imaging system as specifically shown in FIG. 2. Optionally, the stage arm assembly is offset from that of the imaging system, e.g., the stage arm assembly is not aligned with the imaging system. In particular, the inclined biopsy gun and needle do not reside in the field of view of the imaging system so the images are free of biopsy needle artifacts. Offset configurations in which the stage arm assembly is approximately orthogonal to the imaging system are specifically shown in FIGS. 3-7. Some aspects of the stage arm assembly may be consistent with U.S. patent application Ser. No. 12/715,591, titled NEEDLE BREAST BIOPSY SYSTEM AND METHOD FOR USE, filed Mar. 2, 2010, which is incorporated by reference.

A breast support assembly is provided to place the breast in compression. The breast support assembly includes a breast support platform 504 and compression paddle 502 connected to a rotatable platform 500. The platform 500 of the breast support assembly is connected to the support platform 200 via a pivoting connector such as a bearing. Moreover, the stage arm assembly may pivot around a Z-axis which is coincident with Z-axis 302, and a multi-part bearing assembly may be utilized to enable independent rotational movement of the breast support assembly. Optionally, the stage arm assembly pivots about an axis that is offset from Z-axis 302. The compression paddle is linearly movable toward and away from platform 504 in order to compress the breast against the foremost surface of the breast support platform 504 and release the breast from compression upon completion of the procedure. An aperture in the compression paddle allows a biopsy needle to traverse the compression paddle, e.g., in the zero degrees offset configuration. The breast support platform 504 may be integral to a protective cover 506 which encloses the receptor 204. A gap, e.g., 3 cm, between the foremost surface 700 (see FIG. 7) of the breast support platform and the receptor 204 allows the receptor to move during a scan or sweep without interfering with the stationary protective cover and breast support platform. Movement of the receptor during a scan or sweep and the gap enable use of a reduced size receptor. Use of the reduced size receptor enables use of a reduced size foremost surface 700. The breast support platform and/or protective cover may have side-edge sections 702, 704 adjacent to the foremost surface 700 which are angled, curved or otherwise formed away from surface 700 in order provide free space where the protective cover or breast support platform might otherwise interfere with the biopsy gun. For example, and without limitation, use of a 15 cm width receptor and a corresponding size foremost surface allows a side-edge section geometry which facilitates biopsy of relatively thin breasts in the ninety degree offset configuration by avoiding interference between the breast support platform and/or protective cover and the biopsy gun and stage arm assembly. Moreover, the present invention also facilitates access to previously inaccessible lesions, for example, such as those that may be situated in the axilla which prior conventional detectors would be unable to access.

The stage arm assembly 104 and imaging system 102 are independently rotatable for set up, e.g., each through a 180 degree range of arc in the X-Y plane. More particularly, the furthest extent to which the stage arm assembly protrudes from the Z-axis of rotation is less than the minimum distance between the first upright portion of the support arm and the Z-axis of rotation. Consequently, the stage arm assembly can be rotated to either side of the receptor without interference. Similarly, the stage arm assembly can be rotated to either side of the breast support assembly without interference. (compare, e.g., FIG. 3 with FIG. 7) As specifically illustrated in FIG. 2, the stage arm assembly and breast support assembly may also be optionally aligned.

Figure 8:
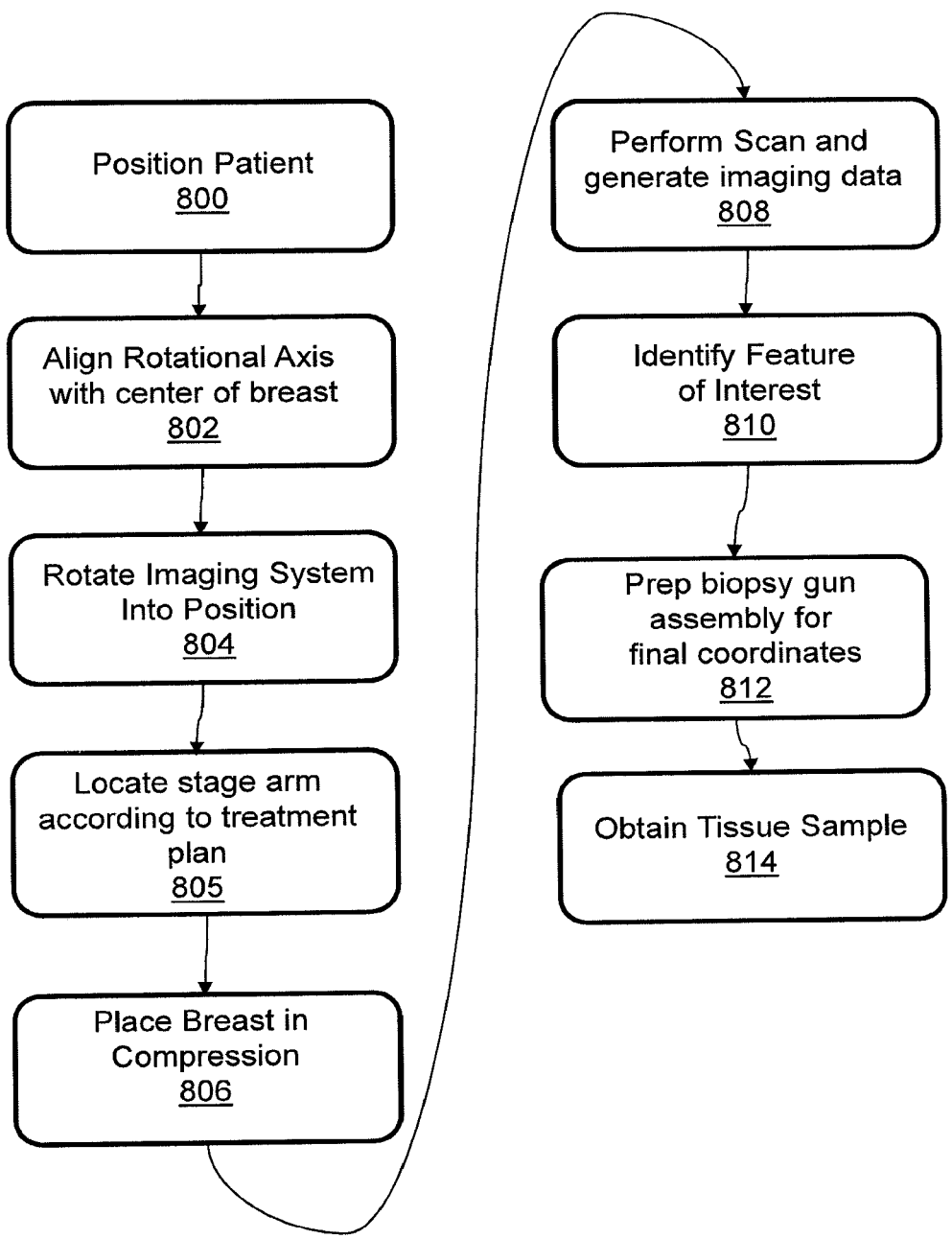
FIG. 8 is a flow diagram of a biopsy procedure.

Some or all of the features described above may be used to facilitate a breast biopsy procedure illustrated in FIG. 8. In order to perform a biopsy procedure the patient is positioned on the table with one or both breasts and possibly one arm protruding through the aperture in step 800. As previously noted, the patient can be oriented in at least two different positions which are offset horizontally by 180 degrees in the X-Y plane. The breast which is the subject of the biopsy procedure may be approximately centered in the Z-axis about which the stage arm assembly and support arm rotate. The equipment support platform may then be moved in one or more dimensions orthogonal to the Z-axis to help center the breast in the axis of rotation in step 802. The imaging system orientation is then adjusted until a desired orientation is obtained for the procedure to be performed, as indicated in step 804. For example, the imaging system may be moved rotationally about the Z-axis, and raised or lowered along the Z-axis. The stage arm assembly orientation is then adjusted for the procedure to be performed, as indicated in step 805. For example, the stage arm assembly may be moved rotationally about the Z-axis and the location of the gun mount on the carriage slide assembly may be adjusted. The patient's breast is then immobilized between a compression paddle and the receptor in step 806. A tomosynthesis scan is performed by moving the x-ray energy source along an arc centered on the top surface of the receptor at step 808. The axis of rotation of the x-ray energy source can optionally be located about 3 cm above the compressed breast, the breast platform, or the top surface of the breast platform. Such an axis of rotation may reduce the amount of blurring in a sweep or movement of the x-ray energy source during a tomosynthesis scan. As an example, at predetermined discrete positions the energy source may be energized to emit a collimated x-ray beam, e.g., at every 1.07° of an arc of +/−7.5°. The motion of the energy source can be continuous or discontinuous. If motion is continuous, a respective set of image data is accumulated over a small increment of continuous motion, e.g., a 0.1° to 0.5° arc of motion of source, although these non-limiting parameters are only an example. Different ranges of motion of the energy source can be used, and the motion of the source may be along an arc centered at a different axis, such as inside the immobilized breast, at the receptor, or elsewhere. During the scan, the x-ray beam irradiates the breast, and radiation that has passed through the breast is received by the receptor. The receptor and associated electronics generate image data in digital form for each pixel of a rectangular grid of pixels at each predetermined discrete angular position of source. An associated three-dimensional image is generated and presented on the display. The image data is used to identify the precise location (final coordinates) of the previously detected feature of interest in step 810. Various fine-adjustment settings may be calculated and used to complete preparation of the stage arm assembly and biopsy gun in step 812. The needle is then actuated in order to obtain a tissue sample in step 814. Any biopsy system may work with the present invention. For example, tubing couples the biopsy needle with a vacuum console and filter for capturing excised tissue samples. The stage arm assembly and other parts of the station may be reconfigured to obtain as many samples as required.

While the invention has been described through the above examples and features, it will be understood by those of ordinary skill in the art that a wide variety of modifications, combinations and variations of the examples and features may be made without departing from the inventive concepts herein disclosed. Moreover, the invention should not be viewed as being limited to any specific purposes described herein, but rather should be viewed as being applicable to accomplish a wide variety of purposes beyond those described herein.

The invention claimed is:

1. An apparatus comprising:
a base;
a table connected to the base, wherein the table is configured to support a patient in a prone position;
an equipment support platform linearly positionable relative to the base and the table;
a tomosynthesis imaging system rotatably secured to the equipment support platform and disposed below the table for imaging a breast of the patient, wherein the tomosynthesis imaging system is rotatable about an axis substantially orthogonal to the table;
a stage arm assembly rotatably secured to the equipment support platform independent of the tomosynthesis imaging system, wherein the stage arm assembly comprises a biopsy needle configured to obtain a tissue sample from the breast of the patient imaged by the tomosynthesis imaging system; and
a breast support assembly linearly positionable along the equipment support platform, wherein the breast support assembly is configured to compress the breast of the patient.

2. The apparatus of claim 1 wherein the axis of rotation of the tomosynthesis imaging system is substantially common with an axis of rotation of the stage arm assembly.

3. The apparatus of claim 2 wherein the equipment support platform is linearly repositionable in at least one dimension orthogonal to the common axis of rotation.

4. The apparatus of claim 3 wherein the tomosynthesis imaging system comprises an x-ray energy source and an x-ray energy receptor, wherein each of the x-ray energy source and the x-ray energy receptor are independently rotatable about the common axis of rotation.

5. The apparatus of claim 2, wherein the table defines an aperture through which the breast imaged by the tomosynthesis imaging system extends.

6. The apparatus of claim 5 wherein the common axis of rotation is aligned with a center of the aperture.

7. The apparatus of claim 2 wherein the tomosynthesis imaging system is rotatable around the common axis of rotation through at least 180 degrees.

8. The apparatus of claim 7 wherein the stage arm assembly is independently rotatable from the tomosynthesis imaging system around the common axis of rotation through at least 180 degrees.

9. The apparatus of claim 8 wherein the table comprises substantially symmetrical end sections and is configured to support the patient in at least two positions which are offset by 180 degrees around the common axis of rotation.

10. The apparatus of claim 1 wherein the tomosynthesis imaging system comprises an x-ray energy receptor disposed within at least a portion of the breast support assembly.

11. An apparatus comprising:
a base;
a table connected to the base, wherein the table is configured to support a patient in a prone position;
a tomosynthesis imaging system rotatably positionable and linearly positionable relative to the base and disposed below the table for imaging a breast of the patient, wherein the tomosynthesis imaging system is rotatable about an axis substantially orthogonal to the table;
a stage arm assembly rotatably positionable and linearly positionable relative to the base and disposed below the table, wherein the stage arm assembly is configured to support a biopsy needle, and wherein the stage arm assembly is rotationally positionable independent of the rotational positioning of the tomosynthesis imaging system; and
a breast support assembly linearly positionable relative to the base, wherein the breast support assembly is configured to compress the breast of the patient, and wherein at least a first portion of the breast support assembly is linearly positionable in a first direction independent of the tomosynthesis imaging system and the stage arm assembly.

12. The apparatus of claim 11, further comprising an equipment support platform movably coupling the tomosynthesis imaging system, the stage arm assembly, and the breast support assembly to the base.

13. The apparatus of claim 12, wherein the equipment support platform is repositionably connected to the base in at least two substantially orthogonal directions.

14. The apparatus of claim 13, further comprising a handle connected to the equipment support platform.

15. The apparatus of claim 13, wherein the table defines an aperture for receiving the breast of the patient.

16. The apparatus of claim 15, wherein a linear range of motion of the equipment support platform is substantially centered on a vertical axis that is aligned with a center of the aperture.

17. The apparatus of claim 11, wherein the first portion of the breast support assembly comprises a compression paddle.

18. The apparatus of claim 11, wherein a portion of the tomosynthesis imaging system is disposed in a second portion of the breast support assembly.

19. The apparatus of claim 11, further comprising a carriage slide assembly connected to the stage arm assembly.

20. The apparatus of claim 19, further comprising the biopsy needle removably secured to the carriage slide assembly.

* * * * *